United States Patent
Ungerank et al.

(10) Patent No.: US 9,770,687 B2
(45) Date of Patent: Sep. 26, 2017

(54) CONTROL OF GAS COMPOSITION OF A GAS SEPARATION SYSTEM HAVING MEMBRANES

(71) Applicant: Evonik Fibres GmbH, Schörfling am Attersee (AT)

(72) Inventors: Markus Ungerank, Perg (AT); Harald Roegl, Wallern an der Trattnach (AT)

(73) Assignee: Evonik Fibres GmbH, Schoerfling am Attersee (AT)

( * ) Notice: Subject to any disclaimer, the term of this patent is extended or adjusted under 35 U.S.C. 154(b) by 265 days.

(21) Appl. No.: 14/442,804

(22) PCT Filed: Oct. 9, 2013

(86) PCT No.: PCT/EP2013/071039
§ 371 (c)(1),
(2) Date: May 14, 2015

(87) PCT Pub. No.: WO2014/075850
PCT Pub. Date: May 22, 2014

(65) Prior Publication Data
US 2015/0336046 A1    Nov. 26, 2015

(30) Foreign Application Priority Data

Nov. 14, 2012  (EP) ..................................... 12192571
May 15, 2013  (EP) ..................................... 13167835

(51) Int. Cl.
*B01D 53/22* (2006.01)
*B01D 63/00* (2006.01)
(Continued)

(52) U.S. Cl.
CPC .......... *B01D 53/22* (2013.01); *B01D 53/226* (2013.01); *B01D 53/228* (2013.01); *B01D 63/00* (2013.01); *C10L 3/104* (2013.01); *C12M 47/18* (2013.01); *B01D 71/64* (2013.01); *B01D 2053/221* (2013.01); *B01D 2256/245* (2013.01);
(Continued)

(58) Field of Classification Search
CPC ............... B01D 63/00; B01D 2311/14; B01D 2317/027; B01D 2257/504; B01D 71/64; B01D 2258/05; B01D 53/228; B01D 53/22; B01D 2256/245; B01D 2053/221; B01D 53/226; C10L 2290/46; C10L 2290/548; C10L 2290/58; C10L 3/104; C12M 47/18; Y02P 20/59; Y02C 10/10
See application file for complete search history.

(56) References Cited

U.S. PATENT DOCUMENTS 4,789,388 A * 12/1988 Nishibata ............... B01D 53/22
                                                      96/381
4,806,132 A    2/1989 Campbell
(Continued)

FOREIGN PATENT DOCUMENTS

EP           0051469 A1    5/1982
WO    WO-2012/000727 A1    1/2012

*Primary Examiner* — Anthony Shumate
(74) *Attorney, Agent, or Firm* — Reed Smith LLP; Matthew P. Frederick; Ryan P. Cox

(57) ABSTRACT

The present invention relates to a method of controlling a gas separation plant, to a plant thus controlled and also to its use for separation of gas mixtures, especially in the processing of biogas or natural gas, or syngas.

20 Claims, 5 Drawing Sheets

(51) Int. Cl.
*C10L 3/10* (2006.01)
*C12M 1/00* (2006.01)
*B01D 71/64* (2006.01)

(52) U.S. Cl.
CPC .... *B01D 2257/504* (2013.01); *B01D 2258/05* (2013.01); *B01D 2311/14* (2013.01); *B01D 2317/027* (2013.01); *C10L 2290/46* (2013.01); *C10L 2290/548* (2013.01); *C10L 2290/58* (2013.01); *Y02C 10/10* (2013.01); *Y02E 50/343* (2013.01); *Y02P 20/59* (2015.11)

(56) References Cited

U.S. PATENT DOCUMENTS

| | | | | |
|---|---|---|---|---|
| 5,053,058 A | | 10/1991 | Mitariten | |
| 5,064,446 A | * | 11/1991 | Kusuki | B01D 53/226 95/53 |
| 5,281,253 A | * | 1/1994 | Thompson | B01D 53/226 95/22 |
| 5,354,474 A | * | 10/1994 | LaPack | B01D 53/22 210/637 |
| 5,383,956 A | * | 1/1995 | Prasad | B01D 53/268 95/45 |
| 5,709,732 A | * | 1/1998 | Prasad | B01D 53/226 95/45 |
| 5,919,285 A | * | 7/1999 | Li | B01D 53/22 95/131 |
| 6,482,251 B1 | * | 11/2002 | Kawasaki | B01D 53/226 95/22 |
| 8,821,614 B1 | * | 9/2014 | Albenze | B01D 53/22 73/37 |
| 2001/0029841 A1 | * | 10/2001 | Li | B01D 53/22 95/45 |
| 2004/0000513 A1 | * | 1/2004 | Colling | B01D 53/225 210/323.1 |
| 2004/0045432 A1 | * | 3/2004 | Yamamoto | B01D 53/22 95/48 |
| 2007/0125537 A1 | * | 6/2007 | Lokhandwala | B01D 53/22 166/291 |
| 2008/0000350 A1 | * | 1/2008 | Mundschau | B01D 53/226 95/56 |
| 2010/0313750 A1 | * | 12/2010 | Sanders, Jr. | B01D 53/22 95/39 |
| 2011/0077446 A1 | * | 3/2011 | Shanbhag | B01D 53/226 585/818 |
| 2012/0102829 A1 | * | 5/2012 | Rothaemel | C10G 29/22 44/447 |
| 2013/0098242 A1 | * | 4/2013 | Ungerank | B01D 53/226 95/51 |
| 2013/0219955 A1 | * | 8/2013 | Yoo | C10L 3/104 62/602 |
| 2014/0033919 A1 | * | 2/2014 | Deckman | B01D 53/0473 95/100 |
| 2014/0360226 A1 | * | 12/2014 | Yoo | C10L 3/104 62/606 |

* cited by examiner

CONTROL OF GAS COMPOSITION OF A GAS SEPARATION SYSTEM HAVING MEMBRANES

CROSS REFERENCE TO RELATED APPLICATIONS

This application is a National Phase filing under 35 U.S.C. §371 of PCT/EP2013/071039 filed on Oct. 9, 2013; and this application claims priority to Application No. 12192571.3 filed in Europe on Nov 14, 2012; and this application claims priority to Application No. 13167835.1 filed in Europe on May 15, 2013. The entire contents of each application are hereby incorporated by reference.

The present invention relates to a method of controlling a gas separation plant, to a plant thus controlled and also to its use for separation of gas mixtures, especially in the processing of biogas or natural gas.

Membranes are known to make it relatively easy to separate gases from each or one another in a pressure-driven process. Although the gases are indeed separated at low cost, purity of the products obtained is usually also low.

Especially when both the components of a binary gas mixture are to be isolated in very pure form, greater expenditure has to be devoted to the technical organization of the membranes and to controlling the process than in the case of a simple single-stage interconnected arrangement where, for example, only the retentate component has to be obtained in a certain purity, while the permeate can be discarded (as with the production of nitrogen from air, for example). This increased expenditure is needed, for example, with the separation of carbon dioxide and methane (e.g. in natural gas or biogas), where methane as a material of value is supposed to ideally end up in the product gas in order that maximum added value may thus be achieved, and is supposed to end up in the off-gas at a very low concentration, if at all, since methane is a greenhouse gas and is not supposed to be passed into the atmosphere. There is a similar scenario with the separation of syngas into carbon monoxide and hydrogen.

A partial pressure difference of each component between the retentate side and the permeate side of the membrane is the driving force of separation in a classic separation of a binary gas mixture with a membrane. For a certain pressure level on the retentate side a certain amount of gas mixture can be driven through the membrane in order to obtain a certain concentration of the slower component in the retentate gas. If, then, the composition of the feed gas changes, the compositions of the retentate gas and of the permeate gas will also change. The system undergoes the same change when the feed gas rate changes. Normally, the concentration changes in the retentate gas and/or permeate gas are taken as the controlled variable and hence either the feed gas rate or the retentate pressure adjusted such that the desired concentration in the permeate and/or retentate is reestablished. Examples of such control regimes are found, for example, in EP 1 324 815, U.S. Pat. Nos. 4,806,132 and 5,281,253.

As mentioned, very pure end products are often isolated using multi-stage interconnected membrane arrangements. Examples thereof are found in WO 2012/000727, U.S. Pat. Nos. 6,565,626 and 6,168,649.

Concentrations in the product streams in a single-stage or retentate-staged two-stage or three-stage interconnected arrangement cannot be set without influencing the two concentrations relative to each other. Changing, for example, the retentate pressure in the retentate product stream (=main or operating pressure of the system), the composition of the permeate changes as well as the composition of the retentate. The same logic applies to changing the feed gas rate.

The use of a three-stage interconnected arrangement as disclosed in the WO2012000727 A1 application separates a mixture of methane and $CO_2$ such that methane is obtained in a yield of above 99% while the purities of the retentate gases and permeate gases distinctly exceed 97%. This process thus separates a gas mixture of two or more components in a three-stage interconnected arrangement such that two components can be isolated in relatively pure form when the gas mixture is a binary mixture. If, however, during this process the composition of the raw gas changes or if a larger or smaller amount of raw gas is to be processed, the composition of the retentate gas and of the permeate gas will change considerably in each case, which is undesirable. Connecting such a gas separation plant to a biogas plant, for example, is accordingly problematic.

This is because if changes in the feed stream are sought to be corrected via a change in the main pressure (=operating pressure, or pressure in the retentate product stream, or retentate product gas pressure), retentate volume flow will also change. This is undesirable in many cases, since the gas in these cases is fed into a transportation line and the latter requires a minimum pressure and often also a minimum and/or maximum volume. There are accordingly some prior art proposals, for example in EP 1 324 815, to install a further compressor in the product stream to regulate the pressure for the transportation line. This is disadvantageous energywise and costly and inconvenient in terms of control technology and therefore commercially unattractive. Furthermore, as explained above, a three-stage interconnected arrangement cannot be used to influence permeate quality independently of retentate quality by adjusting the main pressure.

There accordingly continues to be a great need for gas mixture separation plants and/or control thereof which can be connected to gas sources having varying raw gas composition, pressures and rates and can deliver two or more products in high purity simultaneously, at consistent quality and consistent product gas pressure.

It is an object of the present invention to provide a method of controlling a gas separation plant and a gas separation plant thus controlled where the disadvantages of prior art methods and plants, respectively, are absent or much reduced.

It is a specific object to provide a method and a plant which are each capable of delivering two or more products in high purity simultaneously.

It is a very specific object to provide a method and a plant which are each capable of delivering two or more products in high purity simultaneously even if the raw gas composition and/or pressure and/or volume vary. This plant or method shall more particularly also facilitate the delivery of consistent qualities, i.e. within narrow ranges of variation, preferably in continuous operation.

The method/plant of the present invention shall be particularly flexible in a specific object and retentate and permeate qualities shall be controllable independently of each other. In a very specific object, it shall be possible for the capacity of the plant to be adjusted, for example conformed to changes in the raw gas flow, without having to free up or close down membrane areas, and/or to modulate the main pressure (pressure of the retentate product gas stream), to obtain product gas streams which without additional recompression are useful as a, preferably continuous, feed for a gas transportation line.

The control system of the present invention shall preferably be simple and optionally integratable in existing plants.

Further objects not referred to explicitly are apparent from the overall context of the present description, examples, claims and drawings.

The objects of the present invention are achieved by an apparatus according to claims 1 and 17 and by a method according to claim 9, respectively.

The method of the present invention and the apparatus of the present invention are characterized in that they concern an interconnected membrane arrangement comprising at least a feed stream separation stage (1), a retentate separation stage (2) and a permeate separation stage (3), wherein the second permeate stream (9a+9b) of the retentate separation stage (2) and the third retentate stream (10a+10b) of the permeate separation stage (3) are recycled and mixed with the raw gas stream. By controlling the flow rates of the two streams (9a) and (10a) and hence the permeate pressure of the retentate separation stage (2) and/or the retentate pressure of the permeate separation stage (3), the inventors surprisingly succeeded in achieving the stated objects.

The inventors thereby succeeded in providing a method and a plant in each of which the purities and yields of the product streams of retentate separation stage (2) and of the permeate separation stage (3) can be controlled independently of each other. Very high yields coupled with very good purities are obtainable even in the event of fluctuations in the raw gas stream.

The method of the present invention further makes it possible to keep the main pressure (retentate pressure of retentate separation stage (2)) constant, so the plant of the present invention can be connected to a gas transportation line without additional compression means.

The plant of the present invention is particularly useful for processing raw gas streams from biogas plants. In plants of this type, the amount of raw gas generated and the composition of the raw gas change very often. The fluctuations are readily compensated out by the control provided by the present invention.

The control provided by the present invention is simple and can be integrated in existing gas separation plants.

The method of the present invention is also flexible because two or more different kinds of sensors can be used alone or together. Compositions of streams can be used to control the pressures in the separation stages (2) and (3), as well as flow rates of streams supplied to these separation stages. Notably with the use of flow rate sensors an economical, fast, accurate and simple method is made available after calibration.

Consequently the present invention provides apparatuses according to claims 1 and 17 and a method according to claim 9. Preferred embodiments are protected in the dependent claims.

The present invention will hereinbelow be described in detail. First some important terms will be defined.

The ratio of the permeances of the individual gases determines the selectivity of the membrane with regard to separating two gases and thus indicates how efficiently the membrane is capable of separating a gas mixture with regard to the two components. The term permeate applies to the entire stream generated on the low-pressure side of the membrane, membrane modules or membrane separation step.

Permeate gas refers to the component(s) which the membrane, the membrane module or the membrane separation step each enriches in the permeate stream compared with the respective entry stream.

Retentate refers to the entire stream generated on the high-pressure side of the membrane, membrane modules or membrane separation step and not passing through the membrane.

Retentate gas refers to the component(s) which the membrane, the membrane module or the membrane separation step each enriches in the retentate stream compared with the respective entry stream.

Raw gas/raw gas mixture/raw gas stream (17) refers to a gas mixture of two or more gases and to a stream of this gas mixture which are each to be separated using the method of the present invention and/or the apparatus of the present invention.

Feed stream (5) refers to a gas stream supplied to the feed stream separation stage (1). This stream can correspond to raw gas stream (17), respectively to the raw gas stream compressed by a compressor, at the start of the method. After recycle of the second permeate stream (9b) and of the third retentate stream (10b), the feed stream (5) is composed of the gases of the raw gas stream (17), of the second permeate stream (9b) respectively of the third retentate stream (10b). The feed stream (5) can be obtained by the streams (9b) and (10b) being mixed either both with the uncompressed raw gas stream (17) or both with the compressed raw gas stream or one with the uncompressed and one with the compressed raw gas stream, or by the streams (9b) and/or (10b) being mixed with the raw gas stream (17) in the compressor. Combinations of the versions described above also form part of the subject-matter of the present invention.

Feed stream separation stage (1) refers to a membrane separation stage for separating the feed stream (5) into a first permeate stream and a first retentate stream, (6) and (7), respectively.

Retentate separation stage (2) refers to a membrane separation stage (which may be identical or different in construction to the feed stream separation stage (1)) for separating the first retentate stream (7) into a second permeate stream and a second retentate stream, (9a+9b) and (8), respectively.

Permeate separation stage (3) refers a membrane separation stage (the construction of which can be identical to or different from that of the feed stream separation stage (1) and/or retentate separation stage (2)) for separating the first permeate stream (6) into a third permeate stream and a third retentate stream, (11) and (10a+10b), respectively.

The hereinbelow described preferred and specific embodiments of the method according to the present invention and also the preferred and particularly suitable designs and also the drawings and descriptions of drawings will now be used to provide a merely illustrative further elucidation of the invention; that is, the invention is not limited to these exemplary embodiments and uses or to the particular combinations of features within individual exemplary embodiments.

Individual features indicated and/or depicted in connection with concrete exemplary embodiments are not restricted to these exemplary embodiments or to the combination with the other features of these exemplary embodiments, but can be combined where technically possible with any other versions even though these are not separately discussed in the present document.

Identical reference signs in the individual figures and illustrations of the drawings designate identical or similar components or components acting in an identical or similar manner. The depictions in the drawing also illustrate those features without reference signs, irrespective of whether such features are subsequently described or not. On the other hand, features which are included in the present description but are not visible or depicted in the drawing are also readily apparent to a person skilled in the art.

The present invention relates to an apparatus for separating gases, comprising as membrane separation stages at least a feed stream separation stage (1), a retentate separation stage (2) and a permeate separation stage (3) and also at least one compressor (4) and/or at least one, preferably one or two, vacuum pump(s), wherein said feed stream separation stage (1) separates a feed stream (5), consisting of two or more components, into a first permeate stream (6) and a first retentate stream (7), said retentate separation stage (2) divides said first retentate stream (7) into a second permeate stream (9a+9b), wherein (9a) characterizes the part-stream upstream of said control means (18) and downstream of said retentate separation stage (2) and (9b) characterizes the part-stream downstream of said control means (18), and said part-stream (9b) is supplied to said feed stream (5), and a second retentate stream (8) which is removed as product or further processed, said permeate separation stage (3) divides said first permeate stream (6) into a third retentate stream (10a+10b), wherein (10a) characterizes the part-stream upstream of said control means (19) and downstream of said permeate separation stage (3) and (10b) characterizes the part-stream downstream of said control means (19), and said part-stream (10b) is supplied to said feed stream (5), and a third permeate stream (11), which is removed as product or further processed or discarded.

The apparatus of the present invention is characterized in that said second permeate stream (9a+9b) comprises at least one permeate control means (18) with which the permeate pressure of said retentate separation stage (2) can be raised or lowered and which is controlled on the basis of measured values from one or more measuring means (20a) in said first retentate stream (7) and/or one or more measuring means (20b) in said second retentate stream (8), and/or said third retentate stream (10a+10b) comprises at least one retentate control means (19) with which the retentate pressure of said permeate separation stage (3) can be raised or lowered and which is controlled on the basis of measured values from one or more measuring means (21a) in said first permeate stream (6) and/or one or more measuring means (21b) in said third permeate stream (11).

The method/apparatus of the present invention is notable for being configured such that even with varying compositions or amounts or pressures of the raw gas stream (17) which is supplied to the feed stream (5) together with the second permeate stream (9b) and the third retentate stream (10b), the control provided by the present invention is able to ensure consistent yield and quality for the two product gas streams (8) and (11). It must be emphasized in particular that the purities of product gas streams (8) and (11) can be controlled independently of each other; that is, control over the purity and yield of the two product streams has been successfully decoupled—in contrast to the prior art methods. The control means (18) and (19) used according to the present invention, which are disposed in the return streams (9a+9b) and (10a+10b), are responsible for this.

"Control means" in the context of the present invention are to be understood as meaning devices, structural components, plants or parts of plants which make it possible to raise or lower the pressure in the return streams (9a) and (10a). A nonexhaustive list of possible control means includes: pressure-lowering or pressure-raising valves, gas-depressurizing means, vacuum pumps, blowers, compressing means, especially compressors.

The control means (18) and (19) are regulated with measured values determined by the measuring means (20a), (20b), (21a) and (21b).

In a first preferred embodiment of the present invention, the measuring means (20b) and (21b) determine parameters of product streams (8) and (11) such as, for example, the content of one or more components in the gas streams. The parameters of product gas streams (8) and/or (11) can be determined with the measuring means (20b) and (21b) online or offline, depending on the measuring means used. An online measurement is preferable because regulation can be faster as a result. A person skilled in the art knows suitable measuring means. Preferably, however, they are gas-measuring devices capable of measuring the composition of the gas streams in respect of one or more components, especially inline measuring devices which measure directly in the gas stream (via infrared absorption or sonic speed, density, Coreolis, for example) and external measuring devices according to the same principles of measurement, which take a sample from the stream and measure it either continuously or non-continuously. These have the advantage that the composition can be determined very quickly and is immediately available as an input variable in the control system.

In the event of a variation in the composition of the raw gas or some change in the amount or pressure of the raw gas stream (17) and/or of feed stream (5), the properties, for example the compositions, of product streams (8) and (11) would change in the absence of any counter-control. The measuring means (20b) and (21b) register such changes and initiate a counter-control measure via the control means (18) and (19), so the plant of the present invention can be controlled such that the properties, especially the compositions, of product gas streams (8) and (11) are back in a predetermined range/corridor. The plant of the present invention allows simultaneous control of the two product gas streams (8) and (11), or else keeping just one of the two streams in the predetermined corridor.

In this first preferred embodiment of the present invention, therefore, the present invention provides methods wherein the plant of the present invention is controlled according to one or more of the following alternatives:

i. The concentration of a less readily permeating component B (optionally also determined through a parameter correlating therewith) of said second retentate stream (8) falls below a predetermined setpoint value, the pressure of said second permeate stream (9a) is thus lowered by said permeate control means (18) until said parameter, particularly the desired concentration, is back in the setpoint range.

ii. The concentration of a less readily permeating component B (optionally also determined through a parameter correlating therewith) of said second retentate stream (8) rises above a predetermined setpoint value, the pressure of said second permeate stream (9a) is thus raised by said permeate control means (18) until said parameter, particularly the desired concentration, is back in the setpoint range.

iii. The concentration of a less readily permeating component B (optionally also determined through a parameter correlating therewith) of said third permeate stream

(11) falls below a predetermined setpoint value, the pressure of said third retentate stream (10a) is thus raised by said retentate control means (19) until said parameter, preferably the desired concentration, is back in the setpoint range.

iv. The concentration of a less readily permeating component B (optionally also determined through a parameter correlating therewith) of said third permeate stream (11) rises above a predetermined setpoint value, the pressure of said third retentate stream (10a) is thus lowered by said retentate control means (19) until said parameter, particularly the desired concentration, is back in the setpoint range.

In a second preferred embodiment, the apparatus according to the present invention comprises measuring means (20a) and (21a). The measuring means (20a) and (21a) determine parameters of the first retentate stream (7) and of the first permeate stream (6), respectively, such as the volume flow for example. In this embodiment, it is accordingly not the properties of product streams (8) and (11) which are analyzed, but properties of gas streams supplied to the second/third membrane separation stage.

In the event of a fluctuation in the composition or a change in the amount or pressure of the raw gas stream (17) or of the feed stream (5), this, absent any counter-control, has an effect on the properties, for example the composition or the amounts and pressures, of the first permeate stream (6) and of the first retentate stream (7), respectively. The measuring means (20a) and (21a) register such changes.

Plant calibration makes it possible to correlate these properties of the first permeate stream (6) with those of the third permeate stream (11) (second product stream) and those of the first retentate stream (7) with those of the second retentate stream (8) (first product stream). Therefore, the measuring means (20a) and (21a) can also be used to control the properties, especially the composition and yield, of the two product streams (8) and (11). This is again accomplished using the control means (18) and (19). The control over the compositions of product gas streams (8) and (11) is also decoupled in this embodiment and they can each be regulated independently of each other. Properties of the second retentate stream (8) (first product stream) and of the third permeate stream (11) (second product stream) are to be understood in this case as meaning parameters which can be measured on the particular stream and which the plant of the present invention is to maintain within a certain range or manoeuvre into a certain range. It is particularly preferable for the composition and/or the pressure and/or the rate/volume flow of the particular product streams to be concerned, since these parameters have to be within certain limits for feeding the product gas into a pipeline. These properties/parameters are herein also referred to as properties correlated with the particular volume flow of the first retentate stream (7) or of the first permeate stream (6).

As explained, there first has to be a one-off calibration of the plant in this embodiment of the present invention. However, this initial extra expense and inconvenience is more than compensated by the fact that, after calibration, a simple flow rate measurement of streams (6) and (7) can take place, for example, which is faster and cheaper than, for example, to continuously monitor the composition of product gas streams (8) and (11).

The basic principles of calibration will now be elucidated using a biogas plant with a three-stage interconnected arrangement of the present invention as an example. The apparatus of the present invention can be calibrated as follows:

First, setpoint concentrations are elected for the less readily permeating component B in the third permeate stream (11) and in the second retentate stream (8). Then, the composition, for example, of the raw gas stream (17) is varied and the measuring means (20a) and (21a) are used to determine the changes in the target parameters, the volume flow in this example calibration, of the first retentate stream (7) and of the first permeate stream (8). Concurrently, the measuring means (20b) and (21b), via gas sensors for example, are used to determine the changes in the compositions of the third permeate stream (11) and of the second retentate stream (8). In addition, the permeate pressure of retentate separation stage (2) and the retentate pressure of permeate separation stage (3) are measured. Using the control means (18) and (19), said permeate and, respectively, retentate pressures can be adjusted until the setpoint concentration of component B in the third permeate stream (11) and in the second retentate stream (8) is restored. It is then possible to plot the measured volume flows of the first retentate stream (7) against the permeate pressure of retentate separation stage (2) and the volume flows of the first permeate stream (6) against the retentate pressure of permeate separation stage (3). FIG. 2 shows by way of example how the pressure in the permeate of retentate separation stage (2) has to be adjusted to maintain a consistent concentration for the less readily permeating component B in retentate stream (8). It must be mentioned that the gas composition of the raw gas stream here causes a parallel translocation of the curves. This is also apparent in FIG. 2, where the curve trajectory of the necessary permeate pressure of retentate separation stage (2) as a function of volume flow of the first retentate stream (7) is indicated for three different raw gas compositions (45, 55 and 65% of component B). As can be seen, the result is a separate distinct curve for each raw gas composition.

Where the separation objective is merely to ensure a minimum quality for the less readily permeating component B in the second retentate stream (8), the method of the present invention can be simplified by abstaining from determining various curves for different concentrations of the worse permeant of the raw gas and only using the operating curve with the highest concentration of the more readily permeating component A. Alternatively, only the operating curve with the lowest concentration of the less readily permeating component B can be used. When the concentration of the less readily permeating component B in the raw gas increases, it ought actually be necessary to increase the pressure in the permeate of stage 2 in order that the concentration of the less readily permeating component B in the retentate gas of stage 2 may be kept constant. When the pressure is not adjusted, the concentration of component B in the retentate of stage 2 rises, but will always be above the defined minimum setpoint value on using the calibration line with the lowest concentration of component B in the raw gas.

While two or more curves at different raw gas compositions result in the case of retentate stream (8), the data for the pressures of the retentate of permeate separation stage (3) versus the volume flow of the first permeate stream (6) can be on one curve (see FIG. 3 as an example).

By using the mathematical functions derived for the curves obtained, then, it is possible—solely by measuring the volume flow using the measuring means (20a) and/or (21a)—to ensure rapid control of the plant even without more costly and inconvenient measurement of concentrations in the product streams using measuring means (20b) and (21b), even when the raw gas composition changes or when more raw gas is to be processed.

In case of a varying amount of raw gas it is advantageous for the control means (controller means) of the compressor to receive a signal from a fill level meter in the biogas plant (e.g. gas bag or pressure in the fermenter) or from a sensor in the raw gas stream (17). The compressor can then also be controlled such that the setpoint level of raw biogas is preserved. The plant then regulates itself according to the regulation mechanism described above. Details regarding this preferred embodiment are found hereinbelow.

Flow rate meters (mass or volume) are preferred for use as measuring means (20a) and/or (21a). Parameters can be determined by the measuring means (20a) and (21a) online or offline. An online measurement is preferable. A person skilled in the art knows suitable measuring means.

The present invention in this embodiment accordingly provides methods in which the plant of the present invention is preferably controlled according to one or more of the following alternatives:

v. The volume flow of said first retentate stream (7) (optionally also determined through a parameter correlating therewith) rises above a predetermined setpoint value, the pressure of said second permeate stream (9a) is thus lowered by said permeate control means (18) until the necessary pressure is reached according to the calibration curve and thus the desired property of said second retentate stream (8), preferably the composition of said second retentate stream (8), is back in the setpoint range.

vi. The volume flow of said first retentate stream (7) (optionally also determined through a parameter correlating therewith) falls below a predetermined setpoint value, the pressure of said second permeate stream (9a) is thus raised by said permeate control means (18) until the necessary pressure is reached based on the calibration curve and thus the desired property of said second retentate stream (8), preferably the composition of said second retentate stream (8), is back in the setpoint range.

vii. The volume flow of said first permeate stream (6) (optionally also determined through a parameter correlating therewith) rises above a predetermined setpoint value, the pressure of said third retentate stream (10a) is thus raised by said retentate control means (19) until the necessary pressure is reached based on the calibration curve and thus the desired property of said third permeate stream (11), preferably the composition of said third permeate stream (11), is back in the setpoint range, viii. The volume flow of said first permeate stream (6) (optionally also determined through a parameter correlating therewith) falls below a predetermined setpoint value, the pressure of said third retentate stream (10a) is thus lowered by said retentate control means (19) until the necessary pressure is reached based on the calibration curve and thus the desired property of said third permeate stream (11), preferably the composition of said third permeate stream (11), is back in the setpoint range.

One immense advantage of the plant according to the present invention and of the method according to the present invention resides in the extremely flexible plant capacity, i.e. the ability to vary plant output and to conform it to the demand for product gas. This, as mentioned, can be done without freeing up/closing down of membrane areas. In one preferred embodiment of the present invention, the performance of the plant of the present invention is raised or lowered by changing the volume throughput of said compressor (4), and a resultant change in the concentration of said less readily permeating component B in said second retentate stream (8) is counteracted as per method alternatives i/ii, and/or a resultant change in the concentration of said less readily permeating component B in said third permeate stream (11) is counteracted as per method alternatives iii/iv and/or a resultant change in the flow rate of said first retentate stream (7) is counteracted according to method alternatives v/vi, and/or a resultant change in the flow rate of said first permeate stream (6) is counteracted according to method alternatives vii/viii.

The above-described methods i to viii can be combined with each or one another, and/or hybrid forms can be used. Measuring means (20a), (20b), (21a) or (21b) refers to individual measuring devices, machines, etc., but also combinations or connected assemblies of two or more devices, machines, etc.

The measuring means (20a), (20b), (21a) or (21b) can be combined with each or one another in a flexible way in the various method alternatives. For instance, a measuring means (20a) can be used together with a measuring means (20b) to regulate the permeate control means (18). In this case, there would be a backup measuring system whereby the measuring systems can be checked and counter-checked against each other. In this way it is possible to ascertain, for example, if a measuring means has failed. Corresponding embodiments of the present invention are easily findable from the description and the examples of the present invention by a person skilled in the art, and are also encompassed by the invention.

Depending on the measuring and/or control means used and also the number thereof, it can be advantageous for at least one data-processing means (not shown in the Figures), preferably at least one computer, to be connected inbetween the measuring and control means. This provides easy central control over the apparatus/method of the present invention and a way of logging and coordinating the various measured values/regulating steps. Corresponding technical solutions are commercially available and/or known to those skilled in the art and are co-encompassed by the scope of the present invention.

It is particularly preferable for flow meters to be used as measuring means (20a) and/or (21a) in said first retentate stream (7) and/or in said first permeate stream (6) in the method of the present invention.

It is likewise particularly preferable to use an online or offline measuring means (20b) and/or (21b) in said second retentate stream (8) and/or in said third permeate stream (11) to determine the composition of the particular gas mixture.

In addition to the streams (9a+9b) and (10a+10b) being controlled by the control means (18) and (19), as described above, the present invention also encompasses embodiments in which still further open/closed loop controls are incorporated in the apparatus/method.

In a further preferred embodiment, the apparatus of the present invention comprises a controller means (24) (not shown in the Figures) to regulate the performance of the compressor (4), preferably its rotary speed and hence its volume throughput. A frequency transformer would be an example thereof.

The controller means is preferably used to adjust the performance of the compressor to the amount of raw gas (the production of biogas in a fermenter, for example) to be separated or to the amount of product gas (e.g. methane stream in retentate stream (8)) to be produced. The change in the production amount of raw gas (e.g. raw biogas from a biogas plant) can for example be read off on a fill level indicator of a raw gas intermediate store or at the pressure of the raw gas in a fermenter. When the fill level or the pressure in the fermenter rises, the separation capacity of the membrane separation plant can be increased by increasing the rotary speed of the compressing means. The pressure in the fermenter or the fill level in the intermediate store can thus be kept constant or lowered. If, by contrast, the fill level in the intermediate store or the pressure in the fermenter decreases, the separation capacity of the membrane separation plant can be lowered by reducing the rotary speed of the compressor and thereby the fill level in the intermediate store or the pressure in the fermenter be kept constant or lowered. A change in the feed volume flow (5) as a result of a change in the rotary speed of the compressor would result in a changed composition for the retentate stream (8) and for the permeate stream (11). An immense advantage on the part of the present invention is that this change can be prevented by the closed-loop control mechanisms described above in this invention. By providing this form of control of the plant in respect of the capacity and quality of product gases, then, the present invention makes it possible for the separation capacity of the plant and the composition of product gas streams (8) and (11) to be controlled independently of each other. Therefore, the capacity of the plant can be changed within certain limits via the control means (18) and (19) and the controller means of the compressor without changing the product gas qualities in streams (8) and (11), without having to adjust the retentate pressure in separation stages (1) and (2) and without membrane areas having to be freed up or closed down.

This flexibility in capacity can be restricted to a certain range of compressor speed and hence raw gas volume throughput, which is determined by the design of the plant, especially with regard to pressure in the separation stages, area ratios of membranes in the individual separation stages (1), (2) and (3) and particularly with regard to control means (18) and (19) and their bandwidth in relation to setting the pressure in the respective gas streams (9a) and (10a). If, for example, the minimum possible pressure in permeate stream (9a) is 0.3 bara, then this is the limiting parameter for the feed gas volume flow (5). A further increase in feed gas volume flow (5) would mean that the concentration of the slower component B in retentate stream (8) would fall below the setpoint value and accordingly the desired operating point of the plant could no longer be maintained. The same holds in the event that the pressure in permeate (9a) could not be increased any further than, for example, ambient pressure. This pressure, then, limits the reduction in feed volume flow (5), since a further reduction in feed volume flow (5) would cause the content of the less readily permeating component B in retentate (8) to rise above the setpoint value.

"Controller means" herein is to be understood as referring to the control unit of the compressor, which controls the performance of the compressor, preferably its rotary speed. This controller means can be configured such that it processes measured data from sensors in raw gas stream (17) and/or in upstream stores or production means. For example, the signal from the measuring means can then be used to control a frequency transformer of a compressing means. Appropriate compressors and controller/control means are commercially available and known to those skilled in the art.

The embodiment described above, i.e. compressor performance control and adjustment, can be used to ensure that the separation capacity of the membrane separation plant is conformed to the requirements of raw gas production and/or necessary amounts of product gases (8) and (11). Fluctuations in the gas composition of streams (8) and (11) due to the amount of raw gas (17) to be processed and its composition varying, are compensated out by control means (18) and (19).

In a further preferred embodiment, the apparatus of the present invention is configured such that changing amounts of recycled gas from said second permeate stream (9b) and/or said third retentate stream (10b) are equalized, preferably automatically, by a regulation of the supplied amount of raw gas, from the raw gas stream (17). This occurs particularly preferably without changing the rotary speed of said compressor. This permits the use of simpler and less costly, unadjustable compressors.

The measuring means (22) and (23) employed in this embodiment can be gas sensors, volume or mass flow rate meters or manometers in the second permeate stream (9b) and/or the third retentate stream (10b). The feed rate of raw gas is preferably controlled by a raw gas stream control means (25) in the raw gas stream. The raw gas stream control means has to be capable of replacing the missing quantity (=difference between aspirated amount of compressing means and sum total of recycled streams (9b) and (10b)). This is accomplished for example by constructing the raw gas stream control means as a pressure measurement on the suction side of compressing means (4). A dosage apparatus (e.g. an adjustable analogue valve or a blower or a compressing unit) controlled by this pressure measurement can then maintain a consistent pressure via differently fed quantities of raw gas (17). If the raw gas is under a pressure which conforms to the specifications of the aspirating pressure of the compressor, the raw gas quantity needed in addition to the return streams (9b) and (10b) can also be aspirated directly by the compressor without any additional raw gas control means (17). Again, a data-processing means can be connected between the measuring means (22) and (23) and also raw gas stream control means (25).

In principle, the aforementioned data-processing means may concern different means, i.e. two or more data-processing means can be used in the method of the present invention. These data-processing means can optionally be networked together. Preferably, however, only one central data-processing means is used to centrally supervise and regulate all measuring and control steps.

The apparatus of the present invention, see FIG. 1 by way of example, comprises as mentioned an interlinking of three membrane separation stages at least. Each stage consists of one or more physical gas separation modules which are interconnected in parallel and/or serially within any one stage. The driving force for gas separation in the modules is a partial pressure difference created between the retentate and permeate sides in the respective membrane separation stages. The partial pressure difference is created by a compressor (4), arranged on the feed side of feed stream separation stage (1), and optionally by at least one, preferably one or two, vacuum pump(s) (not depicted in FIG. 1) downstream of the feed stream separation stage (1), preferably on the permeate side of retentate separation stage (2) in the second permeate stream (9a+9b) and/or on the permeate side of permeate separation stage (3) in the third permeate stream (11). It may sometimes be advantageous to use a permeate-side purge gas stream in one or more of the membrane separation stages to create/amplify the partial pressure difference.

In one preferred embodiment of the present invention, a compressor (4) compresses the raw gas mixture, or the gas mixture from the raw gas stream (17) and the second permeate stream (9*b*) and/or the third retentate stream (10*b*), to the desired pressure in the range from 5 to 100 bar, but preferably to a pressure in the range from 9 to 75 bar. If the raw gas stream (17) already has the required pressure, the compressing means (4) need only compress the second permeate stream (9*b*) and/or the third retentate stream (10*b*) to the desired pressure in the range from 5 to 100 bar, but preferably to a pressure in the range from 9 to 75 bar. The resultant feed stream (5) is introduced into feed stream separation stage (1). Feed stream separation stage (1) pre-separates the raw gas mixture into more readily permeating components (permeate gas), which largely pass into the permeate of the first stage, and less readily permeating components (retentate gas), which are predominantly retained by the membrane and build up in the retentate.

In one preferred embodiment, the method/apparatus apparatus of the present invention is configured such that the concentration of at least one permeate gas of said feed stream separation stage (1), after returning said second permeate stream (9*b*) and said third retentate stream (10*b*), is raised in said feed stream (5), preferably by not less than 2%, more preferably by not less than 3% and even more preferably by 3 to 40%, all compared with the concentration in said raw gas stream (17). The degree of increase can depend on the composition of raw gas stream (17) and is particularly marked at low concentrations of a permeate gas (10 to 20%). The concentration increase of one of the permeate gases is preferably between 2 and 15% and more preferably between 3 and 8% when the permeate gas content of raw gas stream (17) is between 30 and 70%. It has turned out that the retentate gas yield of the entire process increases and hence the loss of retentate gas decreases on increasing the concentration of permeate gas in feed stream separation stage (1). For a given stage cut (=ratio of permeate flow to feed flow for stage under consideration), distinctly less permeate gas passes into the permeate of feed stream separation stage (1) when the concentration of at least one component A which permeates more readily in feed stream separation stage (1) or of a permeate gas A is increased in feed stream (5). Similarly, a decrease was observed on reducing the concentration of component A or of a permeate gas A in feed stream (5) to be purified. Thus, stage cut is between 10 and 60%, preferably between 15 and 55% and more preferably between 20 and 50% for a 50% concentration of a component A or of a permeate gas A in feed stream (5) to be purified. In one particularly preferred embodiment of the present invention, the method/apparatus of the present invention is accordingly configured such that the level of permeate gas(es) of feed stream separation stage (1) in feed stream (5) is not less than 40% by volume, preferably more than 50% by volume and most preferably more than 55% by volume, based on the volume of feed stream (5), after recycling the second permeate stream (9*b*) and the third retentate stream (10*b*). This concentration increase for permeate gases in feed stream (5), as explained, serves to increase the efficiency of feed stream separation stage (1), which in turn has the consequence that less retentate gas B passes into the first permeate stream (6). This in turn increases the efficiency of permeate separation stage (3) and ensures that less unwanted retentate gas passes into the third permeate stream (10*a*+b) here too. Notably with the separation of methane-containing raw gases, this leads to the advantage that the unwanted emissions of the greenhouse gas methane were distinctly reduced.

In general, it is preferable for 20 to 100% and more preferable for 40 to 70% of the more readily permeating component A, i.e. permeate gas A, to pass from feed stream (5) into the permeate in feed stream separation stage (1).

The retentate of feed stream separation stage (1) travels—optionally with pressure reduction through an optionally present pressure-reducing valve (12) or with pressure elevation—in the first retentate stream (7) to retentate separation stage (2), where the final purification takes place. The retentate side of retentate separation stage (2), i.e. the second retentate stream (8), preferably sites a pressure-reducing valve (13) (not shown in FIG. 1) with which the main pressure in the system (operating pressure of separation stages (1) and (2)=retentate pressure of stages (1) and (2)) can be maintained and kept constant. The level of the less readily permeating components B, i.e. a retentate gas B, is further increased in retentate separation stage (2) so that the content of component B or of a retentate gas B in the second retentate stream (8) is more than 90%, preferably more than 95% and more preferably more than 97%. In one particularly preferred version, the method/apparatus of the present invention is accordingly characterized in that not less than 95%, preferably not less than 97%, more preferably not less than 99% and most preferably not less than 99.5% of the feed stream separation stage (1) retentate component imported into said apparatus with said raw gas stream (17) is exported via said second retentate stream (8).

The stage cut of retentate separation stage (2) is between 10 and 60% and preferably between 20 and 50% for a 50% concentration of component A or of a permeate gas A in the first retentate stream (7).

The permeate of retentate separation stage (2) is recycled via the second permeate stream (9*b*)—more preferably without portions of permeate stream (9*a* or 9*b*) first being supplied to the first retentate stream (7) downstream of feed stream separation stage (1) and even more preferably completely—and supplied to feed stream (5) and reprocessed. This—as previously explained in connection with the definition of the term "feed stream"—can take place in various ways depending on whether a compressor (4) or even a multi-stage compressor (4) is used. In the case of a one-stage compressor (4), the second permeate stream (9*b*) is preferably supplied to the suction side of compressor (4).

Feed stream separation stage (1) permeate, highly enriched with component A or a permeate gas A is supplied to permeate separation stage (3) via the first permeate stream (6). The retentate control means (19) in the retentate stream of permeate separation stage (3), i.e. in the third retentate stream (10*a*+b), has to be used to stop the pressure of the retentate of permeate separation stage (3) dropping to ambient pressure. In this way, the driving force can be retained for permeate separation stage (3). Permeate separation stage (3) produces a permeate having a more than 95% and preferably more than 97% and even more preferably more than 99%, content of the more readily permeable component A or of a permeate gas A which is exported from the apparatus via the third permeate stream (11). In one particularly preferred embodiment of the apparatus according to the present invention, not more than 5%, preferably not more than 3%, more preferably not more than 1% and most preferably not more than 0.5% of feed stream separation stage (1) less readily permeating component B fed into said apparatus with said raw gas stream (17) is exported via said third permeate stream (11).

Stage cut for permeate separation stage (3) is preferably between 50 and 95% and more preferably between 70 and 93%.

The third retentate stream (10b) is recycled, supplied to feed stream (5) and reprocessed. This can be done in various ways and can depend for example on whether a compressor (4) or even a multi-stage compressor (4) is used. In the case of a single-stage compressor (4), the third retentate stream (10b) is preferably supplied to the suction side of compressor (4) when the aspirating pressure of the compressor is less than the retentate pressure of separation stage (3). When a multi-stage compressor is used, it is preferable to introduce the third retentate stream (10b) into the compressor between two compression stages when the stage pressure of the compressor at the particular stage is less than the retentate pressure of separation stage (3).

In a further preferred embodiment of the method/apparatus of the present invention, it is particularly configured such that the gas volume recycled in said second permeate stream (9b) and in said third retentate stream (10b) amounts in total to less than 60% by volume, preferably 10 to 50% by volume and even more preferably 20 to 40% by volume, of the volume of the raw gas stream (17). The amount of retentate gas streams to be recycled is controlled according to the required purities in product gas streams (8) and (11). The lower the required purities, the smaller the return streams (9b) and (10b). The return streams are very particularly affected by the type and selectivity of the membrane modules used in membrane separation stages (1) to (3). Membrane modules possessing enhanced selectivity bring about a distinct reduction in return streams (9b) and (10b). Similarly, the main pressure in the system (=pressure in separation stages (1) and (2)) influences the amount of recycled gases. The higher the pressure in the system, the smaller the recycled amounts. The ratios of membrane area in the individual stages are a further influence. Larger areas in separation stage (3),
for example, reduce the return stream flow, whereas larger areas in separation stage (2) increase the return stream flows. Therefore, the method/apparatus of the present invention is notable for ensuring the above-detailed increase in the concentration of the permeate component in feed stream (5) despite very small return streams. This leads to a distinct increase in the efficiency of the entire method.

As explained, it is particularly advantageous to use a multi-stage compressor (4). This is because in this case complete decompression of the retentate of the permeate separation stage (3) can be abstained from, since the retentate of permeate separation stage (3) can be fed in between two compression stages of compressor (4). Since retentate separation stage (2) would generally be operated in the selectivity-limited range in the event of decompression to feed pressure, it can be useful for the second permeate stream (9a) to be merely decompressed to a higher pressure level of a multi-stage pressure-increasing unit, i.e. a multi-stage compressor (4), since this reduces the operating costs for the compression unit without significantly worsening the separation outcome. One particularly preferred embodiment of the present invention, therefore, utilizes a multi-stage compressor (4) and supplies gas streams (9b) and (10b) to this compressor between two compression stages in each case.

In one preferred embodiment, the pressure drop across feed stream separation stage (1) is limited to 1 and 30 bar, preferably to 2 and 20 bar and more preferably between 3 and 10 bar. At the same or alternatively, it is preferably ensured that the pressure drop across feed stream separation stage (1) and retentate separation stage (2) is limited to 1 and 100 bar, preferably between 5 and 80 bar and more preferably between 10 and 70 bar.

The apparatus/method of the present invention can in principle be realized with any membrane capable of separating binary gas mixtures or multigas mixtures. Plastics are preferably but not exclusively used as membrane materials. It is particularly preferable to use polyimides, polyamides, polysulphones, cellulose acetates and derivatives, polyphenylene oxides, polysiloxanes, polymers having intrinsic microporosity, mixed matrix membranes, facilitated transport membranes, polyethylene oxides, polypropylene oxides, carbon membranes or zeolites or mixtures thereof as plastics in the separation-active layer.

Particularly preferred membranes include as materials for the separation-active layer, or as a material for the complete membrane, a polyimide of the general formula

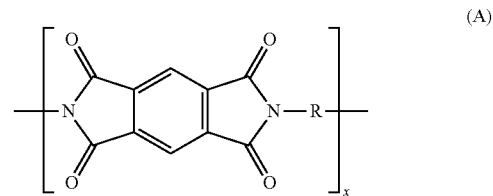

(A)

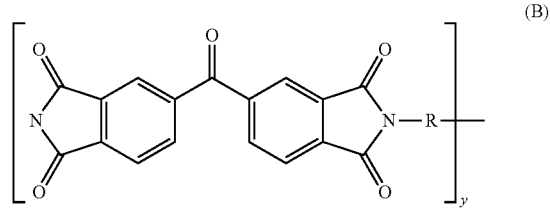

(B)

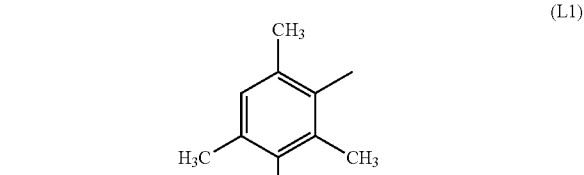

(L1)

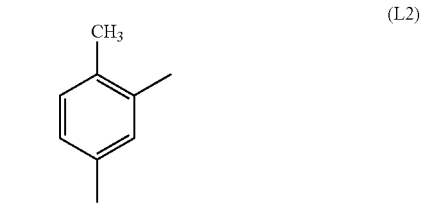

(L2)

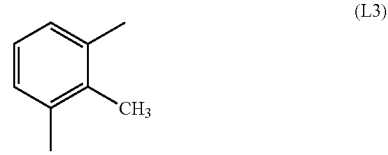

(L3)

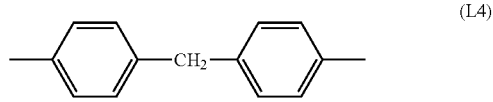

(L4)

where 0≤x≤0.5 and 1≥y≥0.5 and R corresponds to one or more, identical or different radicals R selected from the group consisting of the radicals L1, L2, L3 and L4

It is particularly preferable for a polymer to be concerned where x=0, Y=1 and R is 64 mol % L2, 16 mol % L3 and 20 mol % L4. This polymer is available from Evonik Fibres GmbH under the name P84 or P84 type 70 (CAS numbers 9046-51-9). Specific preference is given to a polymer having the composition x=0.4, y=0.6 and R being 80 mol % L2 and 20 mol % L3. This polymer is availabe from Evonik Fibres GmbH under the name P84HT or P84 HT 325 (CAS numbers 134119-41-8). It is similarly preferable to use mixtures of said polyimides.

Membranes made of the preferred polyimides are available from Evonik Fibres GmbH under the name Sepuran. A process for producing these preferred membranes is disclosed in WO 2011/009919 A1. Membranes disclosed in this Offenlegungsschrift can always be used with preference in the method of the present invention. To avoid pure repetition, the content of this patent application is hereby incorporated herein in its entirety by reference. It was found that these membranes gave the best separation outcomes.

The membranes are preferably used in the form of hollow fibre membranes and/or flat membranes. The membranes are made up into modules which are then used in the separation task. All the gas separation modules known in the art can be used as modules, for example but not exclusively hollow fibre gas separation modules, spiral wound gas separation modules, cushion gas separation modules or tube bundle gas separation modules.

According to the invention, the gas separation membrane modules have a mixed gas selectivity of components A ($CO_2$) and B ($CH_4$) (=ratio of stream A to stream B through the membrane) of not less than 30, preferably not less than 35, more preferably not less than 40, even more preferably of not less than 45 and most preferably of not less than 45 to 80. Membranes of higher selectivity have the advantage that the separation becomes more effective and less permeate has to be recycled from retentate separation stage (2), or less retentate from permeate separation stage (3). Hence, especially when a single-stage compressor (4) is used, less gas has to be compressed twice, which entails economic advantages in the operation of the plant. With very selective membrane modules having a selectivity of 45, only about 35% of the gas imported into feed stream separation stage (1) as raw gas has to be compressed twice, whereas double compression can be up to 300% in the case of a membrane module having a selectivity of just 10. The 35% and 300% are based on tests where a gas mixture with equimolar amounts of components A and B (=feed) was applied and the retentate gas of stage (2) was 98.5% component B and the permeate stream of stage (3) was 99% component B.

It is evident that comparatively selective membranes can make the process of the present invention significantly more economical to run and that the size of the compressor needed and the energy requirements can be reduced.

The method/apparatus of the present invention has more particularly the advantage that it is a pure membrane process and needs no additional clean-up of the permeate and/or retentate streams (11) and (8), respectively, for many applications. For example, in the purification of biogas or natural gas (=removal of carbon dioxide from methane), no pressure swing adsorption or amine scrub is needed any longer for final purification of the retentate, so this can be fed into the natural gas grid.

Furthermore, the method/apparatus of the present invention can be used to produce, at one and the same time, a pure retentate stream (8) and a pure permeate stream (11) in biogas and natural gas purification. It can therefore be released into the atmosphere without great losses of methane and without major impairment of the environment, without any need for further treatment of the gas by a catalytic or thermal afterburn or utilization in a combined heat and power plant. No capital expenditure on further plant facilities is accordingly required, which leads to a more economical purification process for biogas and natural gas.

The apparatus of the present invention is largely already described in WO 2012/000727. The subject matter of WO 2012/000727 is therefore fully incorporated in the description of the present invention by reference.

WO 2012/000727 does not disclose a control system to compensate out fluctuations in the composition or pressure or flow rate of the raw gas stream. WO 2012/000727 merely discloses varying the compressor performance and general pressure ranges to be adhered to if good yields and purities of product gases are to be obtained. The present invention discloses for the first time an open and closed loop control concept of an interconnected membrane arrangement as described in WO 2012/000727, which even permits direct connection of this purification plant to biogas plants providing a variable feed stream. It is accordingly possible to abstain from specific upstream means for providing an approximately constant raw gas stream. The present invention accordingly represents a significant further development of the plant and process of WO 2012/000727. This is particularly true because the control means (18) and (19) and their regulation according to the present invention can be used to ensure a gas quality of streams (8) and (11) which is constant or else varies according to varying requirements, even though the amount of raw gas (17) to be processed and/or the amount of product gases (8) and/or (11) to be produced and/or the raw gas composition change(s). It is advantageous here that to maintain the required gas qualities in streams (8) and (11) the main pressure in the system (=operating pressure in separation stages (1) and (2)) and the membrane areas in separation stages (1) to (3) do not have to be changed.

A further advantage is that the method/apparatus of the present invention has distinctly lower equipment and energy requirements than the known methods of the prior art.

The apparatus/method of the present invention can especially be used for separating gas mixtures comprising two or more gases, in which case it is very particularly preferred for the gas mixture which is separated to be a mixture of predominantly but not exclusively carbon dioxide and methane, or predominantly but not exclusively hydrogen and methane, or predominantly but not exclusively carbon monoxide and hydrogen; or raw biogas or raw natural gas.

The examples which follow are provided by way of further elucidation and description, but not in any way limitation of the present invention.

General Experimental Set-up

Tests were run on a membrane separation plant using a three-stage interconnected arrangement in line with FIG. 1.

Raw gas composition 54% methane, 46% $CO_2$ (=biogas from a biogas plant)

Use of three 2" experimental modules of Sepuran Green (1 module per stage)

Main pressure in the system (=retentate stage (2) pressure) was 17 bara

Air pressure 950 mbara

Permeate pressure of permeate separation stage (3) was 1000 mbara

EXAMPLE 1

The purpose of this test was to find a calibration line with which product gas quality in retentate stream (8) and off-gas quality in permeate stream (11) can be maintained in the event of a change in the feed flow in feed stream (5), or the compressor speed, by changing the permeate pressure of retentate separation stage (2) and by changing the retentate pressure of permeate separation stage (3), respectively.

To this end, compressor performance in a running 3-stage interconnected arrangement as per the general experimental set-up was raised in stages. The pressures of the permeate of retentate separation stage (2) and of the retentate of permeate separation stage (3) were then changed in an attempt to maintain the off-gas concentration (11) and the product gas concentration (8) within a narrow range. As the compressor performance increases from initially 60% to finally 75%, the feed volume flow (5) increases from 3.83 m³/h to 5.23 m³/h, i.e. by 36%. Within this interval, the permeate pressure of retentate separation stage (2) decreases from 951 mbara to 241 mbara and the retentate pressure of permeate separation stage (3) increases from 3.6 bara to 4.43 bara. At all compressor performances, product gas concentration (8) fluctuates between 95.23 and 95.75% methane and the off-gas concentration of methane between 0.5 and 0.62%. Both the values have been regulated within a narrow range, subject to experimental error. Detailed data regarding this test are presented below in Table 1:

TABLE 1

| Compressor performance [%] | Feed stream flow (5) [m³/h] | Permeate stream (9a) pressure [mbara] | Retentate stream (10a) pressure [bara] | Retentate stream (8) c(CH₄) [%] | Permeate stream (11) c(CH4) [%] | Retentate stream (8) flow [m³/h] | Permeate stream (9a) flow [m³/h] | Permeate stream (6) flow [m³/h] | Permeate stream (11) flow [m³/h] | Calculated retentate stream (7) flow [m³/h] |
|---|---|---|---|---|---|---|---|---|---|---|
| 60 | 3.83 | 951 | 3.6 | 95.75 | 0.5 | 1.665 | 0.622 | 1.641 | 1.28 | 2.287 |
| 62.5 | 4.1 | 760 | 3.8 | 95.68 | 0.62 | 1.807 | 0.756 | 1.669 | 1.372 | 2.563 |
| 65 | 4.3 | 660 | 3.9 | 95.54 | 0.58 | 1.907 | 0.838 | 1.715 | 1.427 | 2.745 |
| 67.5 | 4.53 | 560 | 4.03 | 95.23 | 0.62 | 2 | 0.94 | 1.76 | 1.5 | 2.94 |
| 70 | 4.77 | 460 | 4.16 | 95.52 | 0.55 | 2.086 | 1.044 | 1.828 | 1.57 | 3.13 |
| 72.5 | 5.01 | 320 | 4.29 | 95.43 | 0.55 | 2.175 | 1.16 | 1.894 | 1.646 | 3.335 |
| 75 | 5.23 | 241 | 4.43 | 95.34 | 0.62 | 2.267 | 1.28 | 1.925 | 1.697 | 3.547 |

In addition, volume flow was measured for the second retentate stream (8), the first permeate stream (6), the third permeate stream (11) (=off-gas) and the second permeate stream (9a). The volume flows of the first retentate stream (7) can be determined from the sum total of the volume flow values of the second retentate stream (8) and of the second permeate stream (9a).

The permeate pressure of retentate separation stage (2) can then be plotted against the volume flow of the first retentate stream (7) to determine a calibration curve for maintaining product gas concentration when the feed rate of retentate separation stage (2) changes, for example as a result of a change in the compressor speed or as a result of a change in the composition of the raw gas (see FIG. 4).

FIG. 4 shows that a linear regression with good correlation is obtained. This relationship can then be used in a control system for the plant of the present invention. This control system uses a flow value determined for the first retentate stream (7) by means of a volume flow meter (20a) by calculating the permeate pressure as per the straight-line equation in FIG. 4 to determine the permeate pressure required in retentate separation stage (2) to maintain the product gas concentration. This pressure is then appropriately set using a control means (18) in the second permeate stream.

The retentate pressure of permeate separation stage (3) can then be plotted against the volume flow of the first permeate stream (6) to analogously determine a calibration curve for maintaining off-gas concentration in permeate stream (11) when the feed rate of permeate separation stage (3), i.e. the first permeate stream (6), changes, for example as a result of a change in the compressor speed or as a result of a change in the composition of the raw gas (see FIG. 5).

A linear regression with good correlation is also obtained in FIG. 5. This relationship can then be used similarly to the procedure described above for retentate separation stage (2) in a control system for the plant of the present invention. First the flow value of the first permeate stream (6) is determined by measurement with a volume flow meter (21a) and used in the straight-line equation in FIG. 5 to determine the retentate pressure needed in permeate separation stage (3)—and set using the control means (19) in the third retentate stream (10)—to maintain the off-gas concentration in permeate stream (11).

EXAMPLE 2

The issue to be examined is whether, by changing the retentate pressure of permeate separation stage (3), using the control means (19) in the third retentate stream (10), it is possible to achieve a change in the methane concentration in the off-gas from the plant (third permeate stream (11)) and to obtain a calibration curve. In the event that a measurement of the off-gas concentration shows that a change has occurred, it would then be possible to use this calibrated relationship to adjust the methane content of the off-gas.

To this end, while keeping the compressor speed constant, the retentate pressure of permeate separation stage (3) was changed with a control means (19) in the third retentate stream (10) and the resulting change in the methane concentration of the third permeate stream (11) (off-gas) was measured. The volume flows of the plant were also recorded. The values are shown in Table 2.

TABLE 2

| Compressor performance [%] | Feed stream (5) flow [m³/h] | Retentate stream (10a) pressure (bara) | Permeate stream (9a) pressure (mbara) | Permeate stream (11) c(CH4) [%] | Retentate stream (8) flow [m³/h] | Permeate stream (9a) flow [m³/h] | Permeate stream (6) flow [m³/h] | Permeate stream (11) flow [m³/h] | Calculated retentate stream (7) flow [m³/h] | Double compression |
|---|---|---|---|---|---|---|---|---|---|---|
| 60 | 3.3 | 3.5 | 950 | 0.99 | 1.494 | 0.47 | 1.37 | 1.166 | 1.964 | 24.1% |
| 60 | 3.3 | 3.4 | 950 | 0.94 | 1.482 | 0.456 | 1.399 | 1.147 | 1.938 | 25.5% |
| 60 | 3.3 | 3.3 | 950 | 0.88 | 1.462 | 0.44 | 1.434 | 1.122 | 1.902 | 27.7% |
| 60 | 3.3 | 3.2 | 950 | 0.82 | 1.44 | 0.427 | 1.464 | 1.09 | 1.867 | 30.4% |
| 60 | 3.3 | 3.1 | 950 | 0.76 | 1.406 | 0.409 | 1.509 | 1.062 | 1.815 | 33.7% |
| 60 | 3.3 | 3 | 950 | 0.69 | 1.375 | 0.394 | 1.555 | 1.027 | 1.769 | 37.4% |
| 60 | 3.3 | 2.9 | 950 | 0.63 | 1.347 | 0.38 | 1.596 | 0.986 | 1.727 | 41.4% |
| 60 | 3.3 | 2.8 | 950 | 0.56 | 1.283 | 0.36 | 1.663 | 0.955 | 1.643 | 47.5% |
| 60 | 3.3 | 2.7 | 950 | 0.5 | 1.247 | 0.345 | 1.713 | 0.911 | 1.592 | 52.9% |
| 60 | 3.3 | 2.6 | 950 | 0.44 | 1.177 | 0.33 | 1.789 | 0.868 | 1.507 | 61.4% |

As Table 2 shows, the methane concentration in off-gas stream (11) increases as a result of increasing the retentate pressure in permeate separation stage (3). This is shown in graph form in FIG. 6. The regression is linear with very good correlation. This curve can be used as a calibration curve for control purposes. By inserting the desired methane concentration in the equation of FIG. 6 the corresponding retentate pressure required can be determined.

As a point of interest the fast rising double compression rate for a decreasing retentate pressure of permeate separation stage (3) and hence a decreasing methane concentration in the off-gas is depicted in graph form in FIG. 7.

EXAMPLE 3

A change in the permeate pressure of retentate separation stage (2) with a control means (18) in the second permeate stream (9a) can be used to achieve a change in the methane concentration in the product gas of the plant (=second retentate stream (8)). In the event that a measurement of the product gas concentration reveals that a change has occurred, this calibrated relationship can be used to adjust the methane content of the product gas.

To this end, the permeate pressure of retentate separation stage (2) was changed while keeping compressor speed constant, and the resultant change in the methane concentration in the product gas was measured. The values are shown Table 3.

TABLE 3

| Stage 2 permeate pressure [bara] | c(CH₄) in retentate stream (8) [%] |
|---|---|
| 1.005 | 96.44 |
| 0.95 | 96.77 |
| 0.9 | 97.03 |
| 0.85 | 97.23 |
| 0.8 | 97.48 |
| 0.75 | 97.68 |
| 0.7 | 97.93 |
| 0.65 | 98.14 |
| 0.6 | 98.34 |
| 0.55 | 98.55 |
| 0.5 | 98.80 |
| 0.445 | 99.07 |
| 0.4 | 99.28 |
| 0.35 | 99.47 |
| 0.3 | 99.59 |
| 0.284 | 99.66 |

As is apparent, the methane concentration of product gas (8) increases on reducing the permeate pressure in retentate separation stage (2). This is shown in graph form in FIG. 8. The regression is linear with very good correlation. This curve can be used as a calibration curve for control purposes. By inserting the desired methane concentration in the equation of diagram 5, the corresponding permeate pressure required can be determined.

DESCRIPTION OF FIGURES

FIG. 1 shows an inventive arrangement with the recycling of streams (9b) and (10b) onto the suction side of the compressor. Alternative arrangements explained in the above description, for example the recycling of one or more of streams (9b) or (10b) into an elevated compression stage of compressor (4) or without measuring means (22) and (23) or with only some of measuring means (20a) and (20b) and/or (21a) and (21b), are easily derived by a person skilled in the art as a modification of FIG. 1 and therefore are not shown separately. FIG. 1 is merely provided by way of elucidation of the present invention and not in any way as limitation of its scope of protection.

LIST OF REFERENCE SIGNS

Figure 1:
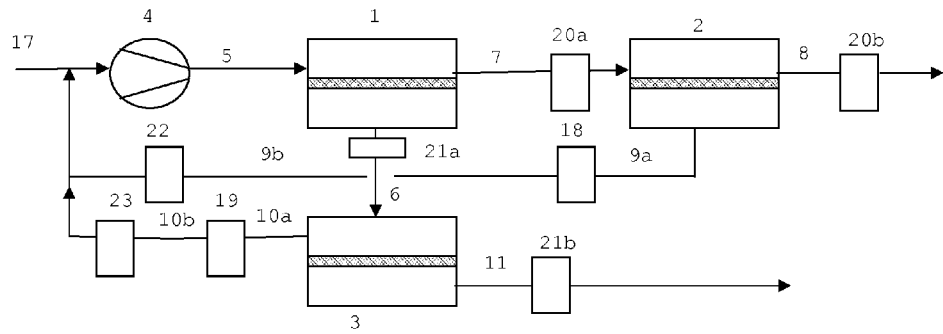
FIG. 1: Exemplary inventive interconnected arrangement comprising measuring means (20a) and (20b), (21a) and (21b), (22) and (23) and also the control means (18) and (19). The control means in raw gas stream (17) and the controller and data-processing means are not shown. However, their arrangement and use is clearly apparent from the overall context of the description.
Figure 2:
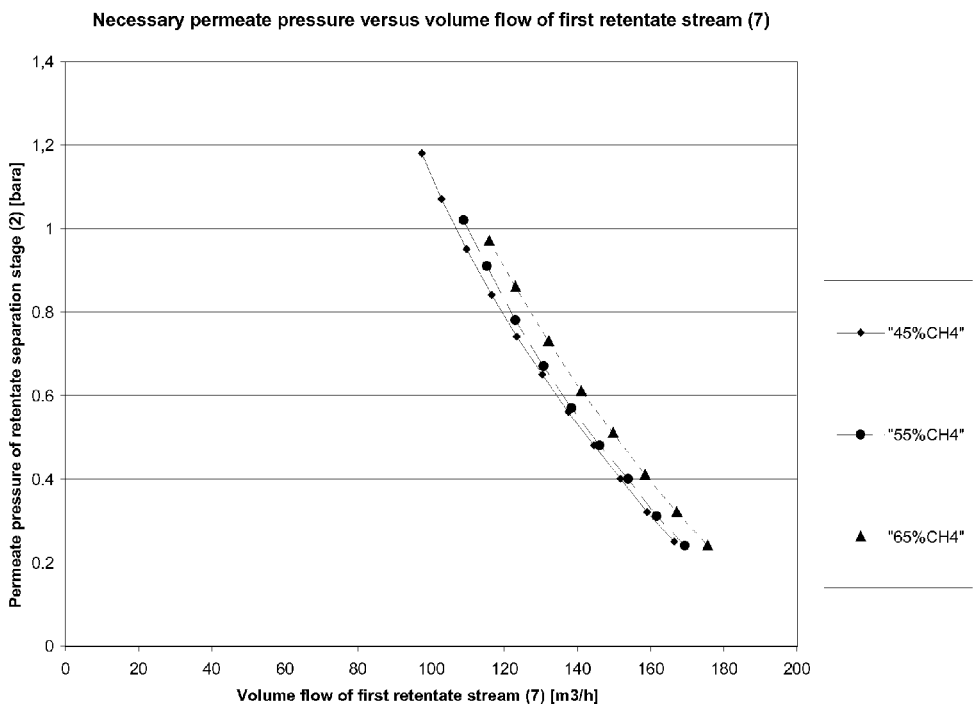
FIG. 2: The permeate pressure needed in retentate separation stage (2) to achieve a retentate quality of 98.3% of component B in the second retentate stream (8) and of 0.7% of component B in the third permeate stream (11) is shown as a function of the volume flow of the first retentate stream (7). The area ratio chosen for the membranes in the membrane separation stages was as follows: stage 1:stage 2:stage 3=2:2:3. Three curves are depicted for different concentrations of component B (CH₄ in this case) of 45, 55 and 65% in raw gas stream (17).
Figure 3:
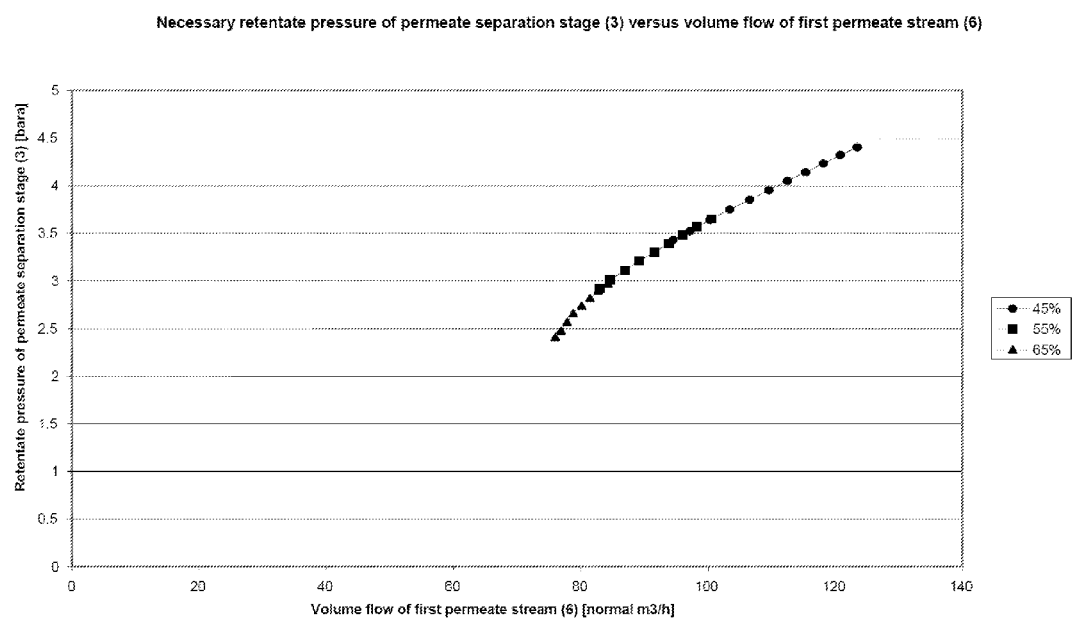
FIG. 3: The retentate pressure needed in permeate separation stage (3) to achieve a retentate quality of 98.3% of component B in the second retentate stream (8) and of 0.7% of component B in the third permeate stream (11) is shown as a function of the volume flow of the first permeate stream (6). The area ratio chosen for the membranes in the membrane separation stages was as follows: stage 1:stage 2:stage 3=2:2:3. Three curves, which merge into each other, are depicted for different concentrations of component B (CH$_4$ in this case)—45%, 55% and 65%—in raw gas stream (17).
Figure 4:
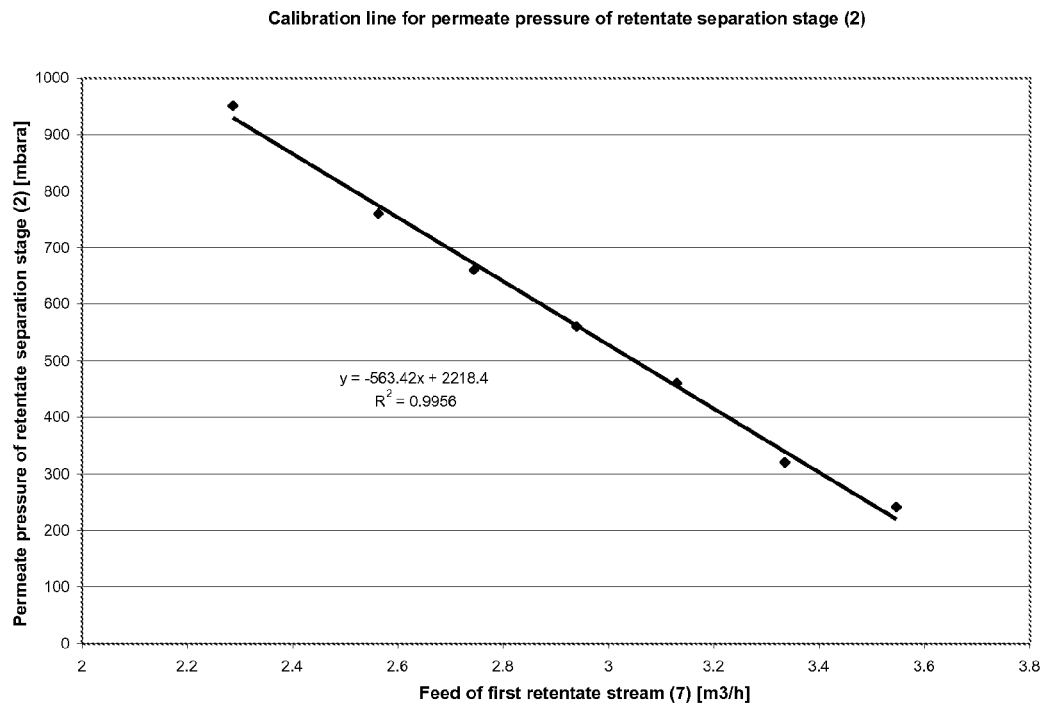
FIG. 4: Dependence of permeate pressure of retentate separation stage (2) on feed gas rate of retentate separation stage (2) to maintain product gas quality
Figure 5:
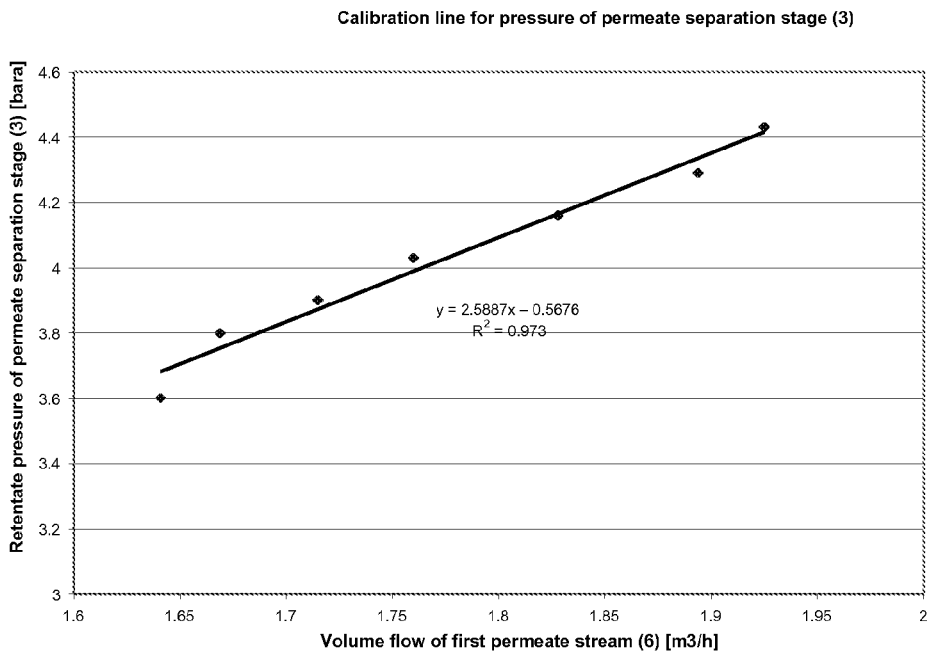
FIG. 5: Dependence of retentate pressure of permeate separation stage (3) on feed gas rate of permeate separation stage (3) to maintain off-gas quality
Figure 6:
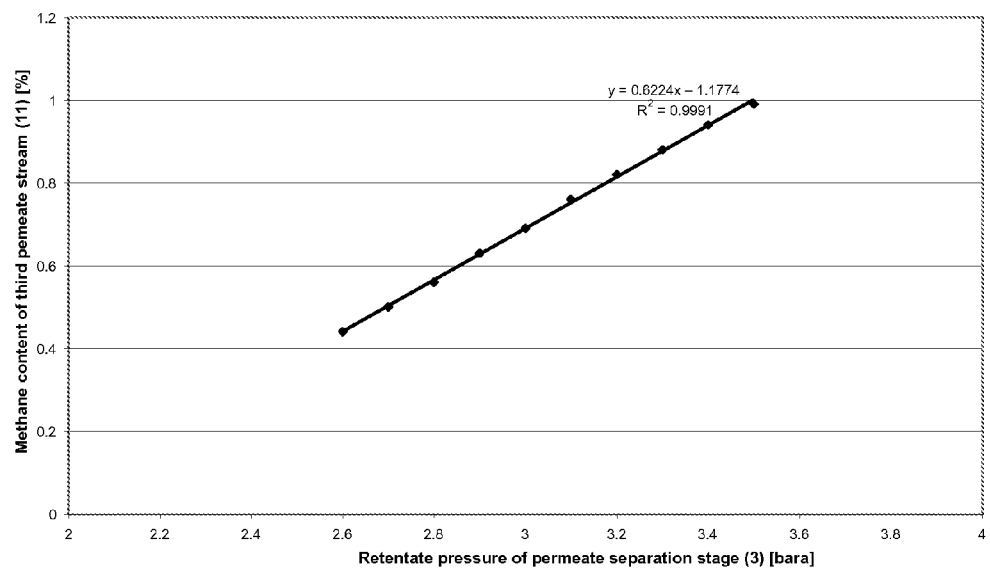
FIG. 6: Dependence of methane concentration in off-gas (11) on retentate pressure of permeate separation stage (3)
Figure 7:
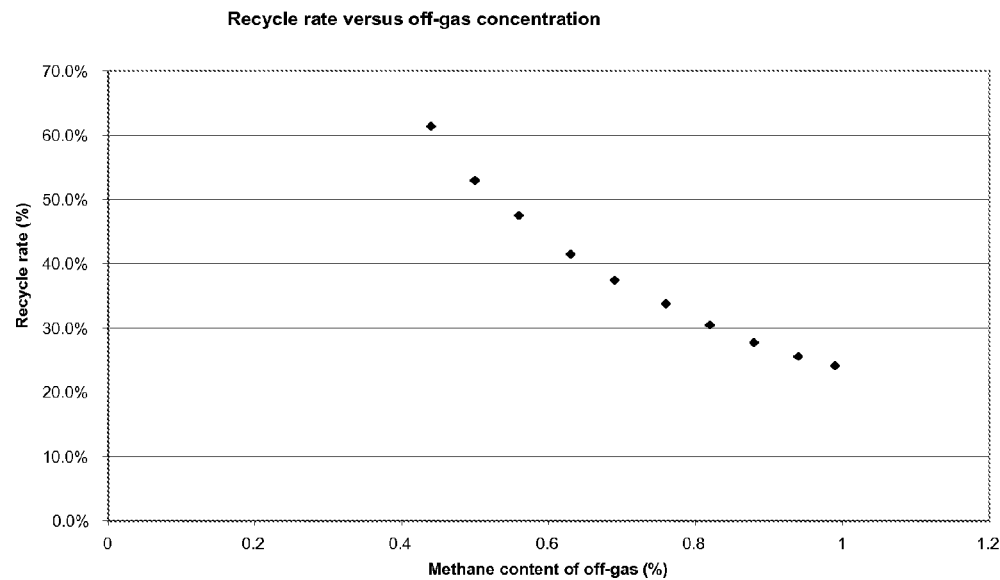
FIG. 7: Dependence of recycling rate on methane content in permeate (11) of permeate separation stage (3)
Figure 8:
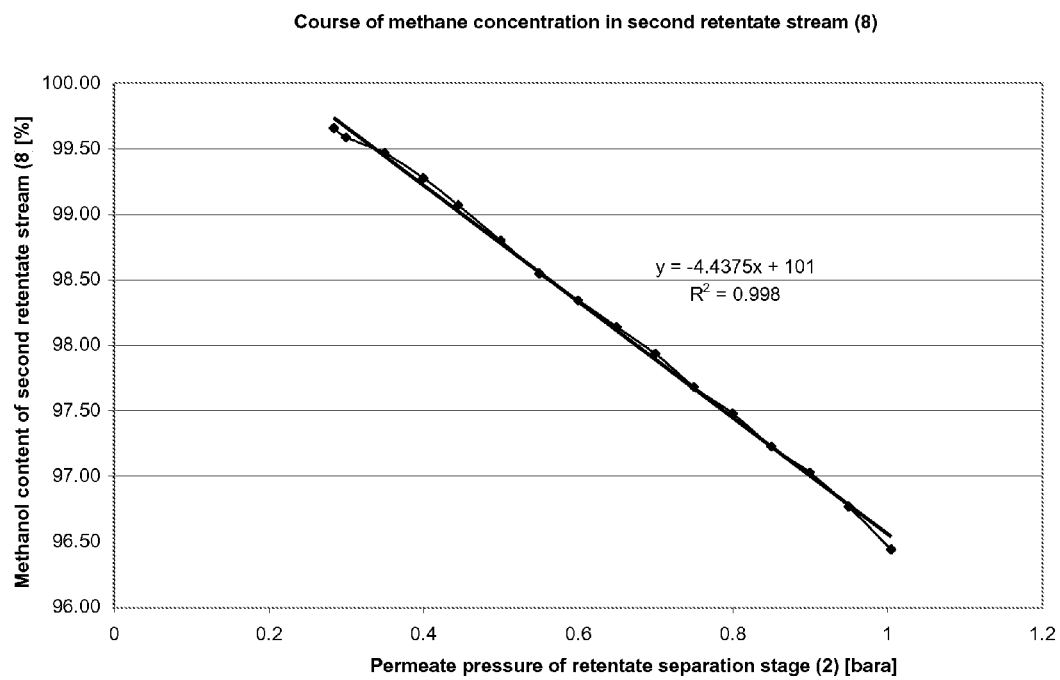
FIG. 8: Dependence of methane concentration in product gas (8) on permeate pressure of retentate separation stage (2)

1: feed stream separation stage
2: retentate separation stage
3: permeate separation stage
4: single-stage or multi-stage compressor
5: feed stream
6: first permeate stream
7: first retentate stream
8: second retentate stream
9: second permeate stream consisting of sub-streams 9a, between control means 18 and retentate separation stage 2, and 9b downstream of control means 18
10: third retentate stream consisting of sub-streams 10a, between control means 19 and permeate separation stage 3, and 10b downstream of control means 19
11: third permeate stream
12: optional pressure-reducing valve in first retentate stream 7 (not shown in the Figures)
13: optional pressure-reducing valve in second retentate stream 8 (not shown in the Figures)
14: optional pressure-reducing valve in third retentate stream 10 (not shown in the Figures)
15: vacuum pump (not shown in the Figures)
16: mixing chamber (not shown in the Figures)
17: raw gas stream
18: permeate control means in 2$^{nd}$ permeate stream (also simply referred to as control means 18 in the description)
19: retentate control means in 3$^{rd}$ retentate stream (also simply referred to as control means 19 in the description)
20a: 1$^{st}$ retentate measuring means for analysis of 1$^{st}$ retentate stream (also simply referred to as measuring means 20a in the description)
20b: 2$^{nd}$ retentate measuring means for analysis of 2$^{nd}$ retentate stream (also simply referred to as measuring means 20b in the description)
21a: 1$^{st}$ permeate measuring means for analysis of 1$^{st}$ permeate stream (also simply referred to as measuring means 21a in the description)
21b: 2$^{nd}$ permeate measuring means for analysis of 3$^{rd}$ permeate stream (also simply referred to as measuring means 21b in the description)
22: 3$^{rd}$ permeate measuring means for analysis of 2$^{nd}$ permeate stream (also simply referred to as measuring means 22 in the description)
23: 3$^{rd}$ retentate measuring means for analysis of 3$^{rd}$ retentate stream (also simply referred to as measuring means 23 in the description)
24: controller means of the compressor (not shown in the Figures)
25: raw gas control means to control the raw gas stream (17) (not shown in the Figures)

The invention claimed is:

1. An apparatus for separating gases, comprising as membrane separation stages at least a feed stream separation stage, a retentate separation stage and a permeate separation stage and also at least one compressor arranged on the feed side of said feed stream separation stage and/or at least one vacuum pump arranged downstream of said feed stream separation stage,
wherein
said feed stream separation stage separates a feed stream, consisting of two or more components, into a first permeate stream and a first retentate stream,
said retentate separation stage divides said first retentate stream into a second permeate stream and a second retentate stream, wherein the second permeate stream is supplied to a permeate control means located downstream of said retentate separation stage and wherein said second permeate stream is supplied to said feed stream downstream of said permeate control means, and wherein said second retentate stream is removed as product or further processed,
said permeate separation stage divides said first permeate stream into a third retentate stream and a third permeate stream, wherein said third retentate stream is supplied to a retentate control means located downstream of said permeate separation stage and wherein said third retentate stream is supplied to said feed stream downstream of said retentate control means, and wherein said third permeate stream is removed as product or further processed or discarded,
said permeate control means can raise or lower the permeate pressure of said retentate separation stage and is controlled on the basis of measured values from one or more measuring means in said first retentate stream and/or one or more measuring means in said second retentate stream,
and/or
said retentate control means can raise or lower the retentate pressure of said permeate separation stage and is controlled on the basis of measured values from one or more measuring means in said first permeate stream and/or one or more measuring means in said third permeate stream.

2. The apparatus according to claim 1, wherein said first permeate stream is not subjected to recompression,
and/or
gas separation membrane modules having a mixed gas selectivity $CO_2/CH_4$ of not less than 30 are used at least in said feed stream separation stage,
and/or
at least one of said membrane separation stages comprises more than one gas separation membrane module interconnected in parallel and/or series,
and/or
the gas separation membrane module(s) consist(s) of hollow fibre membranes and/or flat membranes,
and/or
said apparatus is configured such that the gas volume recycled in said second permeate stream and in said third retentate stream amounts in total to less than 60% by volume of the volume of a raw gas stream,
and/or
said apparatus is configured such that a concentration of at least one permeate gas of said feed stream separation stage, after returning said second permeate stream and said third retentate stream, is raised in said feed stream by not less than 2% as compared with the concentration in a raw gas stream.

3. The apparatus according to claim 2, wherein gas separation membrane modules having a mixed gas selectivity CO₂/CH₄ of not less than 30 are used in all three membrane separation stages.

4. The apparatus according to claim 2, wherein said apparatus is configured such that a concentration of at least one permeate gas of said feed stream separation stage, after returning said second permeate stream and said third retentate stream, is raised in said feed stream by 3 to 40% compared with the concentration in said raw gas stream.

5. The apparatus according to claim 1, wherein
said second permeate stream and said third retentate stream are led to the suction side of said compressor,
and/or in that
the compressor is a multi-stage compressor
and/or
that the compressor is a multi-stage compressor and said second permeate stream and/or said third retentate stream is/are introduced into said compressor between two compression stages,
and/or
in that said compressor is arranged in said apparatus such that it generates a pressure gradient in said feed stream separation stage.

6. The apparatus according to claim 1, wherein
said apparatus comprises a controller means which adapts a rotary speed of said compressor to changes in said second permeate stream and/or said third retentate stream and/or said raw gas stream,
and/or in that
said apparatus is configured such that the supplied amount of raw gas is regulated to adjust to changes in the amount of recycled gas from said second permeate stream and/or said third retentate stream.

7. The apparatus according to claim 1, wherein flow meters are used as measuring means in said first retentate stream and/or in said first permeate stream
or in that
an online or offline measuring means is used in said second retentate stream and/or in said third permeate stream to determine the composition of the particular gas mixture.

8. The apparatus according to claim 1, wherein the membranes in the membrane separation stages comprise a separation-active layer of amorphous or partly crystalline materials chosen from polyimides, polyamides, polysulphones, cellulose acetates and derivatives, polyphenylene oxides, polysiloxanes, polymers having intrinsic microporosity, mixed matrix membranes, facilitated transport membranes, polyethylene oxides, polypropylene oxides and mixtures thereof.

9. The apparatus according to claim 8, wherein the material used for the separation-active layer of the membranes is a polyimide of units of the general formulae A and B:

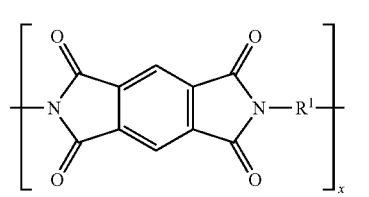
(A)

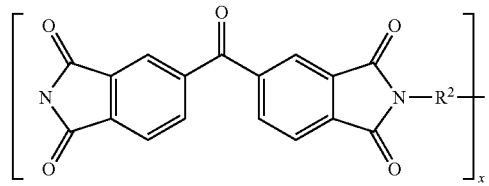
(B)

wherein x is in the range of from 0 to 0.5 and y is in the range of from 0.5 to 1, and wherein R¹ and R² are each independently chosen from one or more of L1, L2, L3 and L4.

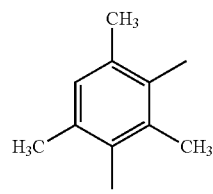
(L1)

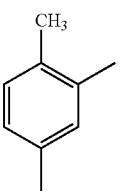
(L2)

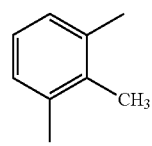
(L3)

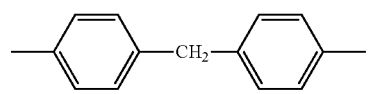
(L4)

10. The apparatus according to claim 1, wherein
not less than 95% of the feed stream separation stage retentate component led into said apparatus is removed via said second retentate stream,
and/or in that
not more than 5% of feed stream separation stage retentate component led into said apparatus is removed via said third permeate stream.

11. A method of controlling a gas separation plant, wherein a gas mixture comprising a more readily permeating component A and a less readily permeating component B is separated in an apparatus according to claim 1, said method comprising
i. selecting a setpoint range for a concentration of said component B in the second retentate stream, or for a parameter correlating with said concentration of component B in the second retentate stream, lowering the pressure of the second permeate stream by the permeate control means until said concentration or parameter correlating with concentration of component B in the second permeate stream is within the setpoint range for component B in the second permeate stream, if the concentration or parameter correlating with concentration for a component B is below the setpoint range in the second retentate stream, and raising the pressure of the second permeate stream by the permeate control means until said concentration or parameter correlating with concentration of component B in the second permeate stream is within the setpoint range for component B in the second permeate stream, if the concentration or parameter correlating with concentration for a component B is above the setpoint range in the second retentate stream;

and/or ii. selecting a setpoint range for a concentration of said component B in the third permeate stream, or for a parameter correlating with said concentration of a component B in the third permeate stream, raising the pressure of the third retentate stream by the retentate control means until said concentration or parameter correlating with concentration of component B in the third retentate stream is within the setpoint range for component B in the third retentate stream, if the concentration or parameter correlating with concentration for a component B is below the setpoint range in the third permeate stream, and lowering the pressure of the third retentate stream by the retentate control means until said concentration or parameter correlating with concentration of component B in the third retentate stream is within the setpoint range for component B in the third retentate stream, if the concentration or parameter correlating with concentration for a component B is above the setpoint range in the third permeate stream.

12. The method according to claim 11, wherein the concentration of component B in the second permeate stream and/or the third retentate stream is determined online and/or offline.

13. A method of controlling a gas separation plant, wherein an apparatus according to claim 1 is used, said method comprising i. selecting a setpoint range for a parameter of the second retentate stream correlated by a calibration curve with a volume flow of the first retentate stream, lowering pressure of said second permeate stream by the permeate control means until said parameter of the second retentate stream is within the setpoint range when the volume flow of first retentate stream increases, and raising pressure of said second permeate stream by the permeate control means until said parameter of the second retentate stream is within the setpoint range when the volume flow of said first retentate stream decreases;

and/or ii. selecting a setpoint range for a parameter of the third permeate stream correlated by a calibration curve with a volume flow of the first permeate stream, raising pressure of said third retentate stream by said retentate control means until said parameter of the third permeate stream is within the setpoint range when the volume flow of said first permeate stream increases, and lowering a pressure of said third retentate stream by said retentate control means until said parameter of the third permeate stream is within the setpoint range when the volume flow of said first permeate stream increases.

14. The method according to claim 13, wherein a calibration curve containing a correlation between a volume flow rate and pressure of a gas stream is used as a control curve to maintain a concentration of a component in a different gas stream.

15. The method according to claim 11, wherein a pressure drop across said feed stream separation stage is set at from 1 to 30 bar, and/or a pressure drop across said feed stream separation stage and said retentate separation stage is set at from 1 to 100 bar.

16. The method according to claim 15, wherein the pressure drop across said feed stream separation stage is set at from 3 to 10 bar, and/or the pressure drop across said feed stream separation stage and said retentate separation stage is set at from 10 to 70 bar.

17. The method according to claim 11, wherein a driving force used for gas separation is a partial pressure difference between a retentate side and a permeate side of at least one of the membrane separation stages, wherein said partial pressure difference is generated by said at least one compressor, which is arranged on the feed side of said feed stream separation stage, and optionally by said at least one vacuum pump in said second and/or third permeate stream and/or by a permeate-side purge gas stream, and/or in that a pressure of the permeate of said feed stream separation stage is in an equal or elevated state relative to an ambient pressure, so there is still a partial pressure difference between a retentate and a permeate of said permeate separation stage and hence there is a driving force in the event that said permeate of said permeate separation stage is at ambient pressure or negative pressure is applied.

18. The method according to claim 11, wherein a controller means adapts a rotary speed of said compressor to changes in the second permeate stream and/or said third retentate stream and/or a raw gas stream, and/or changing amounts of recycled gas from said second permeate stream and/or said third retentate stream are equalized, by a regulation of the supplied amount of raw gas, preferably via a raw gas control means, preferably without changing the rotary speed of said compressor or a performance of the gas separation plant is raised or lowered by changing a volume throughput of said compressor, wherein a resultant change in a volume flow of said first retentate stream is counteracted by selecting a setpoint range for a parameter of the second retentate stream correlated by a calibration curve with a volume flow of the first retentate stream, lowering pressure of said second permeate stream by the permeate control means until said parameter of the second retentate stream is within the setpoint range when the volume flow of first retentate stream increases, and raising pressure of said second permeate stream by the permeate control means until said parameter of the second retentate stream is within the setpoint range when the volume flow of said first retentate stream decreases and/or a resultant change in a volume flow of said first permeate stream is counteracted by selecting a setpoint range for a parameter of the third permeate stream correlated by a calibration curve with a volume flow of the first permeate stream, raising pressure of said third retentate stream by said retentate control means until said parameter of the third permeate stream is within the setpoint range when the volume flow of said first permeate stream increases, and lowering a pressure of said third retentate stream by said retentate control means until said parameter of the third permeate stream is within the setpoint range when the volume flow of said first permeate stream increases.

19. The method according to claim 11, wherein said method is practised in the context of operating a biogas plant, wherein the rotary speed of the compressor and hence the volume throughput of said compressor is controlled according to said biogas plant fill level and/or via fermenter pressure or intermediate store fill level, in order that the fill level in the fermenter and/or intermediate store may be changed or kept constant, or the gas mixture used is chosen from mixtures of predominantly but not exclusively carbon dioxide and methane, predominantly but not exclusively hydrogen and methane, predominantly but not exclusively carbon monoxide and hydrogen, raw biogas, and raw natural gas.

20. A biogas plant comprising an apparatus according to claim 1.

\* \* \* \* \*

UNITED STATES PATENT AND TRADEMARK OFFICE
CERTIFICATE OF CORRECTION

PATENT NO. : 9,770,687 B2
APPLICATION NO. : 14/442804
DATED : September 26, 2017
INVENTOR(S) : Markus Ungerank and Harald Roegl It is certified that error appears in the above-identified patent and that said Letters Patent is hereby corrected as shown below:

In the Claims

Claim 13, Column 27, Line 65:
"increases." should read --decreases.--

Claim 18, Column 29, Line 11:
"permeate stream increases." should read --permeate stream decreases.--

Signed and Sealed this
Twentieth Day of February, 2018

Andrei Iancu
*Director of the United States Patent and Trademark Office*